(12) United States Patent
De Vries

(10) Patent No.: US 9,517,119 B2
(45) Date of Patent: Dec. 13, 2016

(54) MOUTHPIECE FOR CLEANING TEETH WITH AN ADJUSTABLE ARC LENGTH AND/OR ARC WIDTH

(71) Applicant: KONINKLIJKE PHILIPS N.V., Eindhoven (NL)

(72) Inventor: Johannes Hotze Bernhard De Vries, Haren (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 290 days.

(21) Appl. No.: 14/366,203

(22) PCT Filed: Dec. 17, 2012

(86) PCT No.: PCT/IB2012/057397
§ 371 (c)(1),
(2) Date: Jun. 17, 2014

(87) PCT Pub. No.: WO2013/093764
PCT Pub. Date: Jun. 27, 2013

(65) Prior Publication Data
US 2014/0352087 A1    Dec. 4, 2014

Related U.S. Application Data

(60) Provisional application No. 61/579,000, filed on Dec. 22, 2011.

(51) Int. Cl.
*A61C 17/22* (2006.01)
(52) U.S. Cl.
CPC .................................. *A61C 17/228* (2013.01)
(58) Field of Classification Search
CPC ......... A61H 13/00; A46B 9/045; A46B 13/00; A46B 13/02; A46B 13/023; A61C 17/16; A61C 17/22; A61C 17/222; A61C 17/32; A61C 17/34; A61C 17/3409; A61C 17/3445; A61C 17/3454; A61C 17/3463; A61C 17/3472; A61C 17/3481; A61C 17/349; A61C 17/228
(Continued)

(56) References Cited

U.S. PATENT DOCUMENTS 5,177,827 A * 1/1993 Ellison ................... A61C 17/26
15/22.1
5,365,624 A * 11/1994 Berns ................. A61C 17/0211
15/22.1
(Continued)

FOREIGN PATENT DOCUMENTS

DE            3437191    *  5/1986
KR      20040103255 A    12/2004
(Continued)

*Primary Examiner* — Mark Spisich

(57) ABSTRACT

The mouthpiece includes an arcuate base assembly (12), comprising two side pieces (14, 16) and an intermediate center piece (18), the two side pieces (14, 16) being connected rotatably to opposing ends of the center piece (18), such that the rear ends of the side pieces move outwardly and inwardly. A flexible screw thread spindle (30) having two side portions and a front portion is connected at the free ends thereof (33, 35) to the rear ends of the side pieces of the base assembly, such that the flexible spindle member follows the arcuate shape of the base assembly. Two side carriages (40, 42) are mounted on opposing side portions of the spindle (30), the carriages having bristles (43) mounted thereon for cleaning teeth. A motor and gear box assembly (36) are mounted at the front of the appliance for moving the two carriages along the respective side portions of the spindle (30), which have opposing screw threads. A front carriage (48) is mounted on and moves along a front spindle by a front motor and gear box (36).

9 Claims, 3 Drawing Sheets

(58) Field of Classification Search
USPC ..... 15/22.1, 22.2, 167.2; 433/103, 114, 118, 433/131, 216; 601/140, 142
See application file for complete search history.

(56) References Cited

U.S. PATENT DOCUMENTS

| | | | |
|---|---|---|---|
| 7,537,451 B1 | 5/2009 | Ramnarine | |
| 8,584,291 B2 * | 11/2013 | Thompson | A61C 17/228 15/22.1 |
| 2011/0185525 A1 | 8/2011 | Stapelbroek et al. | |
| 2011/0289709 A1 * | 12/2011 | Attaway | A61C 17/228 15/167.2 |

FOREIGN PATENT DOCUMENTS

| | | | |
|---|---|---|---|
| WO | 2008142600 A1 | | 11/2008 |
| WO | 2009/048287 | * | 4/2009 |
| WO | 2010076695 A1 | | 7/2010 |
| WO | 2011021109 A1 | | 2/2011 |

* cited by examiner

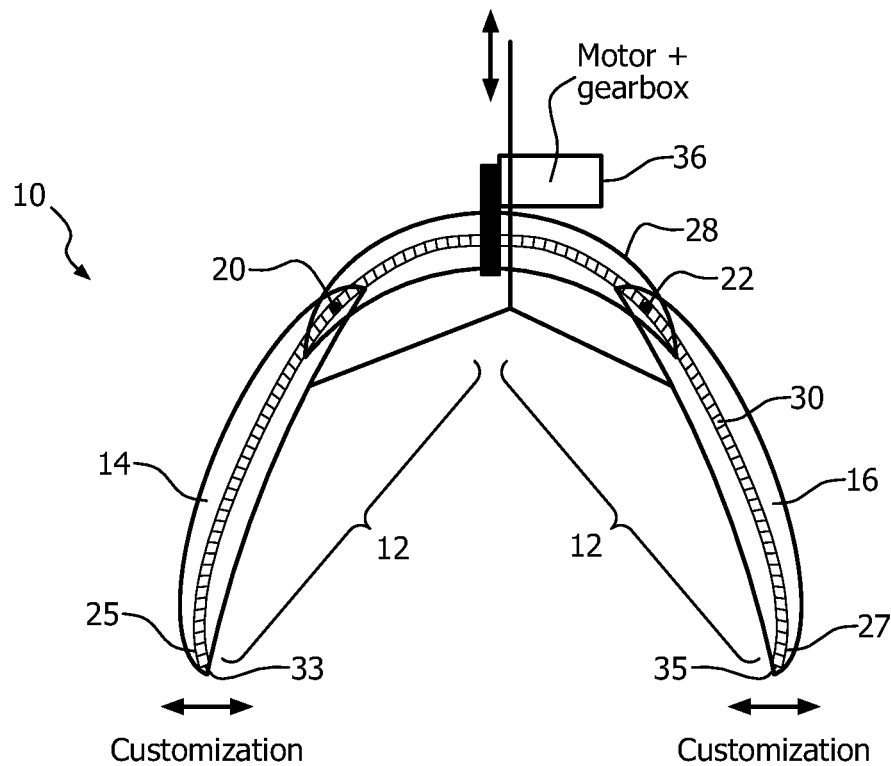
FIG. 1
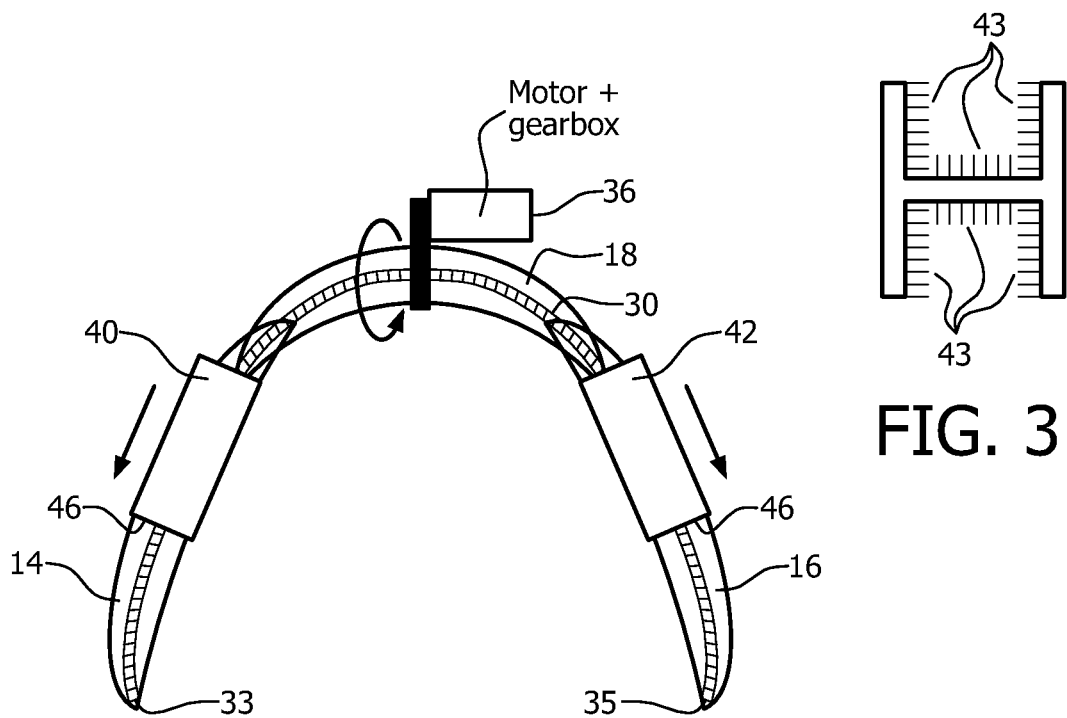
FIG. 2
FIG. 3

16

MOUTHPIECE FOR CLEANING TEETH WITH AN ADJUSTABLE ARC LENGTH AND/OR ARC WIDTH

This application claims the benefit or priority of and describes relationships between the following applications: wherein this application is a Section 371 U.S. National Stage Application of International Application No. PCT/IB2012/057397, filed Dec. 17, 2012, which claims the priority of U.S. Provisional patent application 61/579,000 filed Dec. 22, 2011, all of which are incorporated herein in whole by reference.

This invention relates generally to mouthpiece appliances for cleaning teeth, and more particularly concerns a mouthpiece with an adjustable structural geometry.

Mouthpiece appliances for cleaning teeth are known and have the advantage of an inherent capability of effective, fast cleaning, in which all surfaces of all the user's teeth are consistently and evenly cleaned at once, without any requirement of control by the user. Consistent cleaning is easier achieved with a mouthpiece appliance than, for instance, a toothbrush, including power toothbrushes. Mouthpiece appliances for teeth cleaning present some challenges in implementation, however, including effective driving of the cleaning portion of the appliance, and the accommodation of a range of oral geometries. Oral geometry of users can vary in width, i.e. from side to side, as well as length, i.e. from front to rear.

Various ways to customize a mouthpiece to a user's oral geometry are known, including cutting the mouthpiece to the right length, or using material for the mouthpiece which can be softened in boiling water and then fitted to the user's oral geometry, but these are generally disfavored by consumer, as indicated by tests and focus groups. Another way to effectively customize a mouthpiece to fit individual geometries is by a dental professional taking a scan of the dental geometry of the user and then fitting or adapting the mouthpiece to that configuration. The disadvantage of this system, while actually effective in customization, is that professional involvement is necessary, which includes a significant additional expense and is time consuming.

Accordingly, it is desirable to have a mouthpiece arrangement which is readily customizable by a user to accommodate the user's oral geometry, particularly different widths and lengths.

Accordingly, the mouthpiece for cleaning teeth comprises: an arcuate-shaped base assembly having two side portions and an intermediate central portion wherein forward ends of the two side portions are connected rotatably to opposing ends of the central portion, such that rear ends of the side portions are moveable outwardly and inwardly, providing an adjustable width for the mouthpiece; a first flexible screw thread spindle member connected at the free ends thereof to the rear ends of the side portions of the base assembly so as to maintain the spindle in an arcuate shape similar to the shape of the base assembly; two side carriages mounted on opposing sides of the spindle member, the side carriages having teeth cleaning members mounted thereon; and a drive assembly for driving the two side carriages along the opposing sides of the spindle, cleaning the teeth.

FIG. 1 is a top view of a part of the mouthpiece system described and claimed herein.

FIG. 2 is a top view of the system of FIG. 1 shown with two cleaning members.

FIG. 3 is a cross-sectional diagram of a cleaning member portion of the system of FIG. 2.

Figure 4:
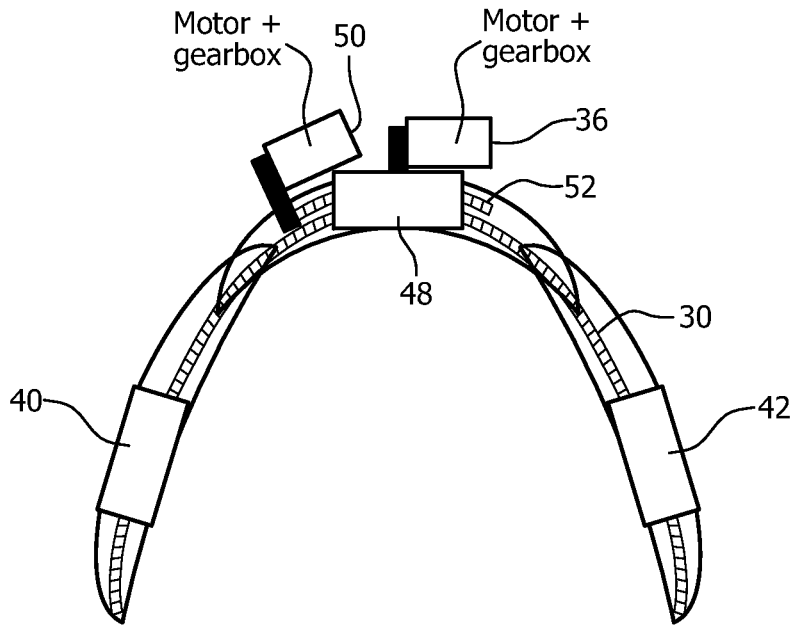
FIG. 4 is a top view of a mouthpiece system which includes two side cleaning members and a front cleaning member.
Figure 5:
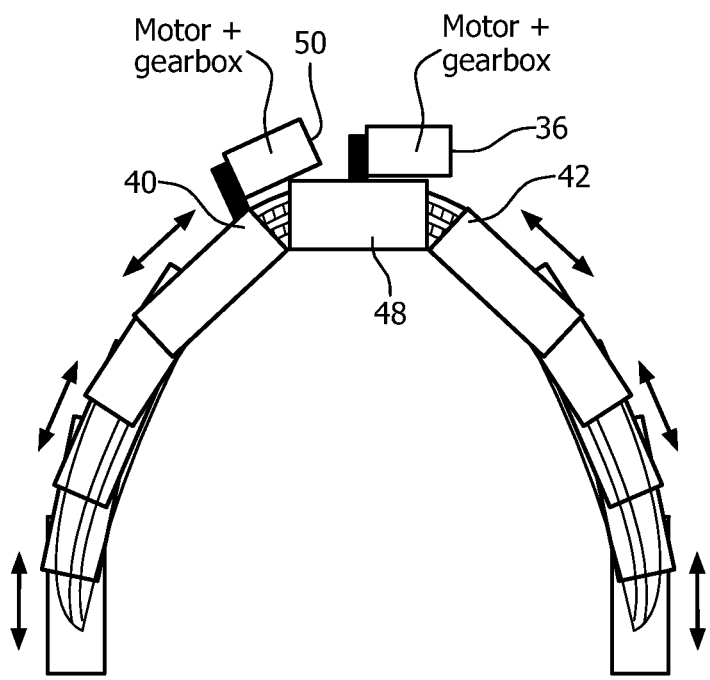
FIG. 5 is a top view showing the movement of the side cleaning during operation of the appliance.
Figure 6:
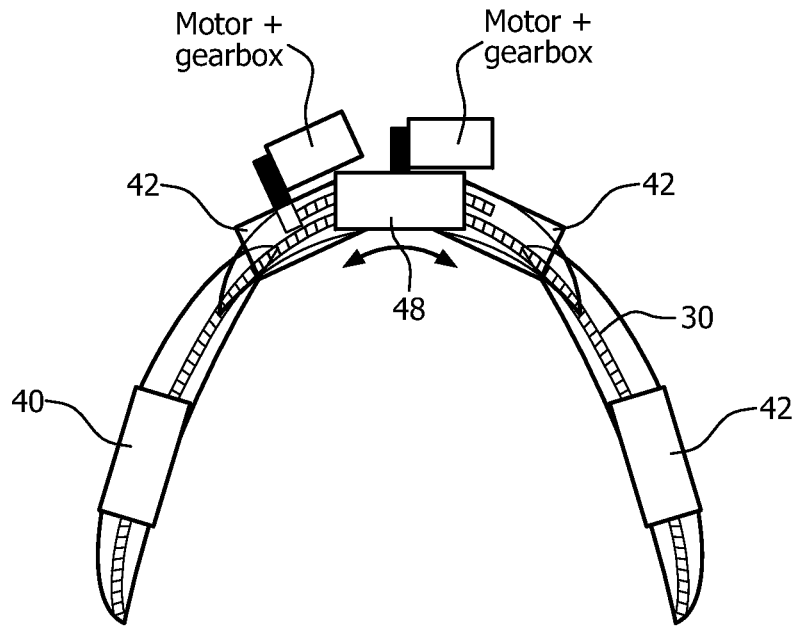
FIG. 6 is a top view showing movement of the front cleaning member during operation of the appliance.

FIG. 1 is a top view of a mouthpiece, for cleaning teeth, the cleaning portion of which is designed to fit within the mouth of a user. The mouthpiece, shown generally at 10 in FIG. 1, includes a base assembly 12. The base assembly 12 in the embodiment shown comprises three rigid members 14, 16 and 18. Rigid members 14 and 16 are positioned on opposing sides of the mouthpiece and are associated with the side dental regions of the mouth, while intermediate rigid member 18 is positioned between the two side members 14 and 16 and is associated with the front dental region. The two side members 14 and 16 are connected to the opposing ends of the intermediate rigid member by hinges 20, 22, or similar members, which permit rotation of the side members from side to side. This movement of the side base members permits customization (change) for the width of the oral geometry, as shown by the arrows adjacent rear ends 25 and 27 of the base members 14 and 16.

The three base members form the structural foundation for mouthpiece 10. In the embodiment shown, the two side base members are made from a rigid material, are flat and are typically approximately 0.5 inches wide over most of their length and 0.1-0.3 inches thick, although these dimensions can vary. The intermediate base member also is approximately 0.5 inches wide and 0.1-0.3 inches thick. The three base members can vary in their exact peripheral configuration. One arrangement is shown in the several figures.

A flexible spindle 30 is mounted on base assembly 12. Spindle 30 comprises a screw thread with the screw thread on one side of the mouthpiece being threaded in one direction, and on the other side threaded in the opposing direction. The flexible spindle in the embodiment shown has a diameter of approximately ⅛ inch and is connected at the opposing free ends 33, 35 thereof to the rear ends of the two side members in order to maintain the arcuate shape of the spindle, so that it substantially follows the configuration of the base assembly.

A motor and gearbox assembly 36 is connected to the spindle to drive the threaded spindle and is mounted to the base assembly at the very front of the mouthpiece. The motor and gearbox assembly, connected both to the spindle and the base assembly, assists in maintaining the configuration of the spindle relative to the base assembly, i.e. so that it conforms to the shape of the base assembly, as shown most clearly in FIG. 1.

When the motor runs, the screw thread on one side of the mouthpiece will turn in one direction, while the screw thread on the other side of the mouthpiece will turn in the other direction. FIG. 2 shows cleansing carriages 40, 42 mounted on the opposing two sides of the spindle 30, which is attached at its ends to the rear ends of their associated side base members, as noted above, such that the spindle follows the shape of the base member assembly. In the embodiment shown, each cleaning carriage is approximately 1 inch long and 0.7 inches wide and 1 inch tall. The side carriages typically clean the molar regions of the teeth. The carriage has a cross-sectional shape of an H as shown in FIG. 3, with cleansing bristles 43 arranged on the inside surfaces of the H. The bristles are adapted to clean the surfaces of the teeth;

the H configuration of the carriage results in the bristles mechanically contacting and cleaning the teeth in both the upper and lower jaws at the same time, including the side surfaces and the flat top surfaces of the teeth. It should be understood that while the carriages in the embodiment shown have bristles for cleaning teeth, other teeth cleaning arrangements can be used including pads or other similar cleansing elements. The carriages 40, 42 are moved on the spindle such that the rearmost end[s] of the carriages 46 and moves beyond the end of the spindle by a certain amount of the length of the carriage, up to ⅔ of the length.

This arrangement provides the customization capability for different lengths of the appliance. As indicated above, the width customization capability is achieved by the base member/spindle arrangement in which the side members can be easily moved outwardly/inwardly, relative to the front member, to fit the user's particular oral geometry.

The appliance also typically, but not necessarily, includes a front carriage 48, as shown in FIG. 4. The front carriage 48 is similar in arrangement to the side carriages 40 and 42. It is arranged to move along a separate front spindle 52 to clean the front teeth. The front carriage is moved by its own separate motor and gear box arrangement 50. The front carriage 48 is thus driven independently of the two side carriages 40 and 42, on its own spindle. The arrangement of FIG. 4, with two side carriages, movable along spindle 30, and front carriage 48, movable along spindle 52, is the preferred arrangement, since it completely covers all of a user's teeth.

Proper operation of the mouthpiece requires grounding the appliance during operation, as follows. When front carriage 48 is fixed and not moving (not cleaning), it provides the grounding capability for movement of the side carriages 40 and 42, which travel along the respective spindle side portions by virtue of the operation of the motor gear box 36. The side carriages move along their separate routes in a sinusoidal or oscillatory pattern. Typically, each of the side carriages will cover (brush) a short distance, for instance 1 cm or so at one location, and then translate physically to a next portion of the spindle, where they again oscillate over a short distance. This continues until the entire travel distance is covered and all the molar teeth are brushed. Alternatively, the side carriages can cover the entire travel distance in one oscillation. The frequency of oscillation is relatively low, typically in the range of ½ to 5 Hz, for instance.

As indicated above, in the next stage of the mouthpiece operation, the side carriages remain fixed and provide grounding for the movement/operation of the front carriage, which brushes the front teeth as it oscillates back and forth over the front teeth at a similar frequency to the side carriages, ½-5 Hz. The operational arrangement between the movement of the front carriage and the two side carriages is such that the total movement of the side carriages will overlap to some extent the movement of the front carriage.

The result of the mouthpiece operation is that the entire oral (teeth) geometry of the user is brushed/cleansed thoroughly and consistently. Again, one significant advantage of a mouthpiece is that no teeth are inadvertently missed, such as by poor brushing techniques by the user, and all the teeth are cleaned approximately equally. This eliminates the disadvantage of operator control where inevitably some areas of the mouth do not receive appropriate, detailed cleaning. The base assembly/spindle arrangement shown overcomes a significant disadvantage of conventional mouthpieces, in that it conveniently provides a desired customization capability for an individual user for both width and length of the mouthpiece.

Figure 7:
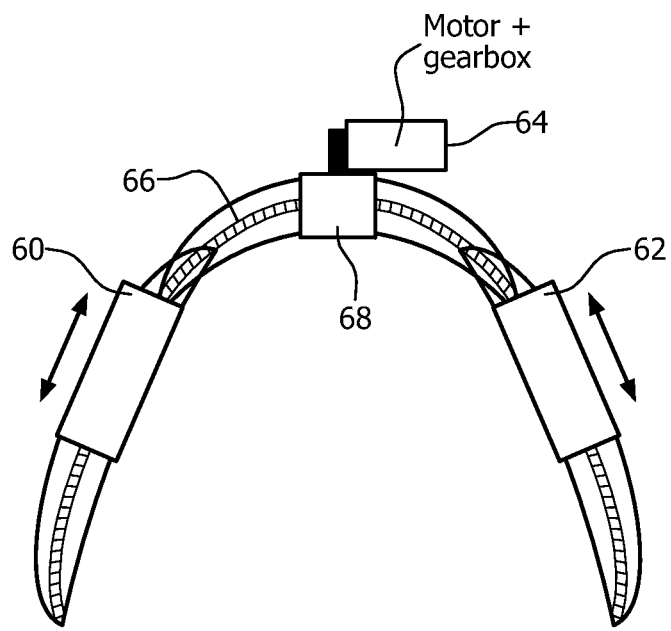
FIG. 7 is a top view of another embodiment of the mouthpiece system.

It should be understood, referring to FIG. 7, that two carriages 60, 62 could be used with a single motor/gear box 64 positioned at the very front of the mouthpiece, moving on a single spindle 66. In this arrangement, there is a fixed grounding member 68 positioned at the front teeth, with the two side carriages covering nearly all the teeth from the rearmost molars to the front teeth. A very small central part of the front teeth region will remain unbrushed. It is preferable that three carriages be used, to provide complete coverage of all of the teeth in the oral geometry.

Accordingly, a mouthpiece has been disclosed which uses a combination of a rigid base plate and a flexible screw thread spindle along with a plurality of cleaning carriages, which by a motor and gear box are capable of consistently cleaning all of the teeth in a single operation. The arrangement of the screw thread flexible spindle, with screw threads moving in opposing directions along the two sides, provides the desired drive arrangement. The front teeth are cleaned with a front carriage moving on a front spindle.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. A mouthpiece for cleaning teeth, comprising:
an arcuate-shaped base assembly having two side portions and an intermediate central portion wherein forward ends of the two side portions are connected rotatably to opposing ends of the central portion, such that rear ends of the side portions are moveable outwardly and inwardly, providing an adjustable width for the mouthpiece;
a first flexible screw thread spindle member connected at the free ends thereof to the rear ends of the side portions of the base assembly so as to maintain the spindle in an arcuate shape similar to the shape of the base assembly;
two side carriages mounted on opposing sides of the spindle member, the side carriages having teeth cleaning members mounted thereon; and
a drive assembly for driving the two side carriages along the opposing sides of the spindle, cleaning the teeth.

2. The mouthpiece of claim 1, wherein the side carriages are configured and arranged to extend beyond the end of the first spindle member by a selected amount when the side carriages reach the free ends of the first spindle member, thereby providing an adjustable length for the mouthpiece, depending upon how far the carriages extend.

3. The mouthpiece of claim 1, including a front carriage moving on a second screw thread spindle member mounted to the base assembly at the front of the mouthpiece, and an associated motor and drive assembly for moving the front carriage back and forth across the front teeth along the second spindle member, the front carriage also having teeth cleaning members mounted thereon.

4. The mouthpiece of claim 3, wherein the carriages have a cross-sectional shape in the form of an H, to clean the side surfaces and upper and lower surfaces of the teeth in both the upper and lower jaws.

5. The mouthpiece of claim 3, wherein the travel of the two side carriages along the first flexible screw thread member and the travel of the front carriage along the second screw thread spindle are arranged so as to provide an overlap between coverage of the two side carriages and the front carriage.

6. The mouthpiece of claim 1, wherein the first screw thread spindle has a first screw thread portion for one side of the mouthpiece in one direction, and a second screw thread portion for the other side of the mouthpiece in the opposing direction.

7. The mouthpiece of claim 1, wherein the base assembly is made from rigid material.

8. The mouthpiece of claim 1, including a separate fixed grounding member positioned at the front of the mouthpiece.

9. The mouthpiece of claim 1, wherein the drive assembly for the side carriages is mounted to the base assembly.

* * * * *